(12) United States Patent
Bunker et al.

(10) Patent No.: US 8,810,644 B2
(45) Date of Patent: Aug. 19, 2014

(54) THERMAL INSPECTION AND MACHINING SYSTEMS AND METHODS OF USE

(75) Inventors: Ronald Scott Bunker, Waterford, NY (US); Jason Randolph Allen, Niskayuna, NY (US); Jared Crosby, Scotia, NY (US)

(73) Assignee: General Electric Company, Niskayuna, NY (US)

( * ) Notice: Subject to any disclaimer, the term of this patent is extended or adjusted under 35 U.S.C. 154(b) by 409 days.

(21) Appl. No.: 12/968,308

(22) Filed: Dec. 15, 2010

(65) Prior Publication Data

US 2012/0154570 A1 Jun. 21, 2012

(51) Int. Cl.
*H04N 7/18* (2006.01)
*F01D 5/00* (2006.01)
*G01N 25/18* (2006.01)
*G01N 25/72* (2006.01)
*G01N 21/95* (2006.01)
*F01D 5/14* (2006.01)

(52) U.S. Cl.
CPC ............... *F01D 5/005* (2013.01); *G01N 25/18* (2013.01); *G01N 25/72* (2013.01); *G01N 21/951* (2013.01); *F01D 5/14* (2013.01)
USPC .............. 348/86; 73/204.11; 382/152; 703/2; 374/43

(58) Field of Classification Search
CPC ..... G01N 25/72; G01N 25/18; G01N 21/951; F01D 5/14; F01D 5/005
USPC ...................... 348/86; 250/341.1; 374/43, 45; 73/204.11
IPC ........................................................ H04N 7/18
See application file for complete search history.

(56) References Cited

U.S. PATENT DOCUMENTS

| | | | |
|---|---|---|---|
| 4,644,162 A | 2/1987 | Bantel et al. | |
| 5,111,046 A | 5/1992 | Bantel | |
| 6,570,175 B2 | 5/2003 | Bales et al. | |
| 6,585,408 B2 | 7/2003 | El-Gabry et al. | |
| 6,732,582 B2 | 5/2004 | Bunker et al. | |
| 7,388,204 B2 | 6/2008 | Key et al. | |
| 2003/0128736 A1 | 7/2003 | Dalio et al. | |
| 2004/0225482 A1* | 11/2004 | Vladimirov et al. | 703/2 |
| 2005/0173636 A1* | 8/2005 | Beyer | 250/341.1 |
| 2006/0256837 A1 | 11/2006 | Clifton et al. | |
| 2009/0016402 A1* | 1/2009 | Bunker et al. | 374/43 |
| 2009/0201971 A1* | 8/2009 | Goldammer et al. | 374/45 |
| 2009/0255332 A1* | 10/2009 | Bunker et al. | 73/204.11 |
| 2009/0297336 A1 | 12/2009 | Allen et al. | |
| 2010/0250155 A1 | 9/2010 | Bunker et al. | |

* cited by examiner

*Primary Examiner* — Jay Patel
*Assistant Examiner* — Neil Mikeska
(74) *Attorney, Agent, or Firm* — Scott J. Asmus

(57) ABSTRACT

The present application provides a thermal imaging and machining system for a machine component. The thermal imaging and machining system may include a machining subsystem with a machining device for drilling one or more holes in the machine component and a thermal inspection subsystem positioned about the machining subsystem. The thermal inspection subsystem may include an imager and one or more fluid supply lines such that a thermal response of the holes in the machine component may be determined.

18 Claims, 2 Drawing Sheets

THERMAL INSPECTION AND MACHINING SYSTEMS AND METHODS OF USE

TECHNICAL FIELD

The present application relates generally to thermal inspection and machining systems and methods of use thereof and more particularly relates to integrated thermal inspection systems with associated machining systems for automated drilling and inspection of cooling holes in turbine components and the like and methods of use thereof.

BACKGROUND OF THE INVENTION

Hot gas path components, such as gas turbine airfoils and the like, generally employ advanced cooling techniques so as to withstand extremely high operating temperatures. These advanced techniques may include the use of film cooling. Film cooled components typically are inspected using manual pin checks and the like. Pin checks generally involve the use of undersized pin gages and/or water flow visualization. Such water flow visualization techniques involve flowing water through the component and having an operator visually verify that the water is flowing from each film hole. These manual approaches, however, are qualitative and subject to operator interpretation.

Infrared inspection techniques have the potential to perform quantitative, objective inspection of the film cooled components in a largely automated fashion. Infrared inspection systems and current airflow check systems, however, typically may have conflicting technical requirements such that separate infrared inspection and airflow check systems may be used. Such separate use may be time consuming and at considerable expense.

Both infrared inspection systems and airflow check systems generally are used after all or most of the film holes in the component in question have been drilled or otherwise machined and completed. As a result, the component may need to be returned to the drill or other device for further machining if, for example, an improperly drilled film hole or the like is detected, Moreover, hole breakthrough detection during drilling often is difficult, particularly with laser drilling into a cooling passage. Multiple inspection, transport, and machining steps thus may be required with the use of known machining equipment and inspection techniques.

There is thus a desire for improved thermal inspection systems, machining systems, and methods of use so as to reduce the number of machining, transport, and inspection steps while improving overall component quality. Such improved systems and methods may provide a quality component while avoiding the time and subjective results found in known manual operations. Likewise, such improved systems and methods may provide a quality component in less time and with less operator involvement for reduced overall cost.

SUMMARY OF THE INVENTION

The present application thus provides a thermal imaging and machining system for a machine component. The thermal imaging and machining system may include a machining subsystem with a machining device for drilling one or more holes in the machine component and a thermal inspection subsystem positioned about the machining subsystem. The thermal inspection subsystem may include an imager and one or more fluid supply lines such that a thermal response of the holes in the machine component may be determined.

The present application further provides a method of machining and inspecting a machine component. The method may include the steps of maintaining a steady flow rate and/or pressure of a fluid through the machine component, drilling at least one hole within the machine component, determining whether a change in the flow rate and/or the pressure has been detected, flowing the fluid at a first temperature and then at a second temperature through the machine component, imaging the at least one hole within the machine component, and determining if a thermal response of the at least one hole within the machine component meets a predetermined range of values.

The present application further provides a thermal imaging and machining system for a hot gas path component. The thermal imaging and machining system may include a machining subsystem with a drilling device for drilling one or more holes in the hot gas path component and a thermal inspection subsystem positioned about the machining subsystem. The thermal inspection subsystem may include an infrared camera, a hot air line, and a cold air line such that a transient thermal response of the holes in the hot gas path component may be determined.

These and other features and improvements of the present application will become apparent to one of ordinary skill in the art upon review of the following detailed description when taken in conjunction with the several drawings and the appended claims.

DETAILED DESCRIPTION

Figure 1:
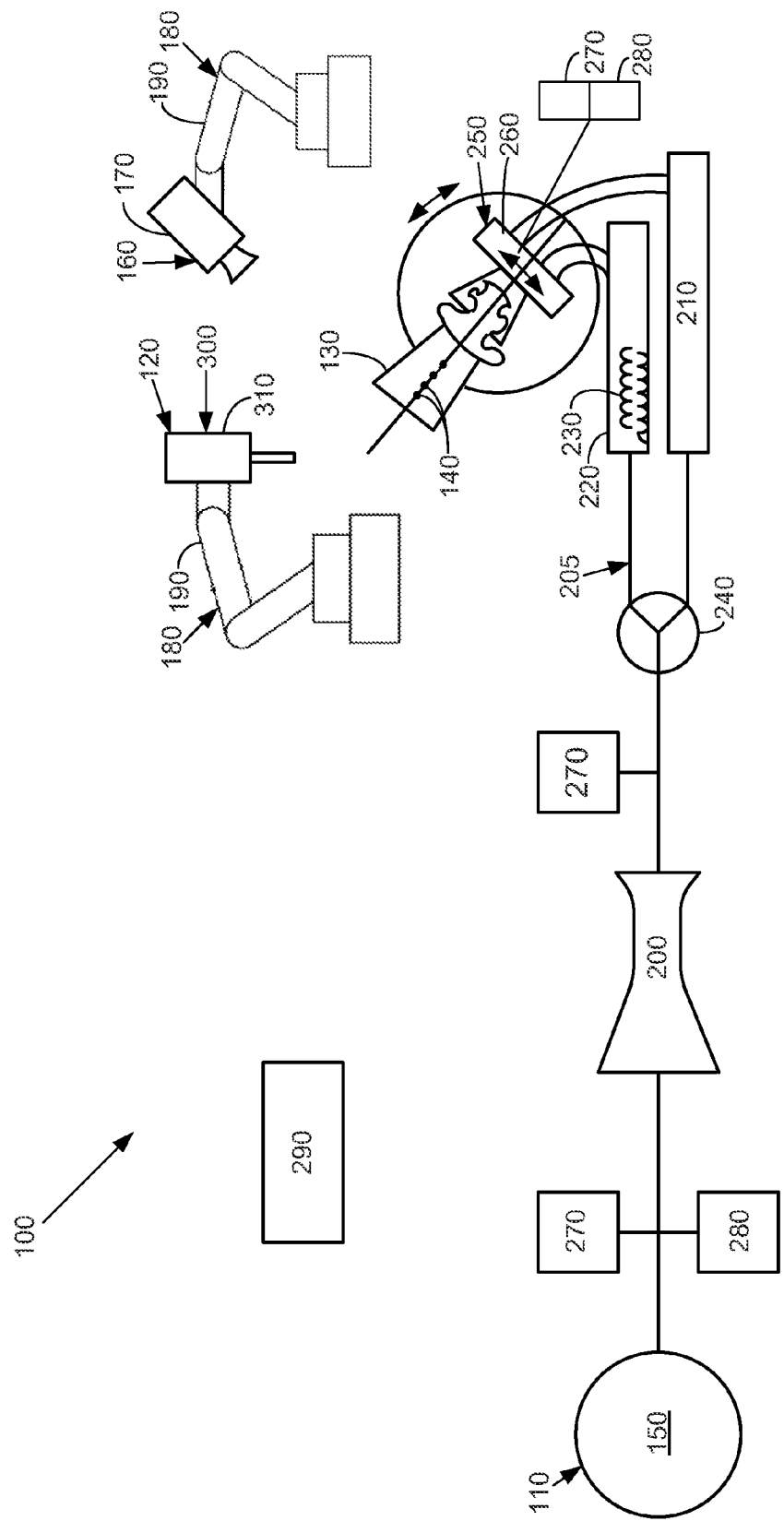
FIG. 1 is a schematic view of a thermal inspection and machining system as may be described herein.

Referring now to the drawings, in which like numerals refer to like elements through out the several views, FIG. 1 shows a thermal inspection and machining system 100 as may be described herein. The thermal inspection and machining system 100 may include a thermal inspection subsystem 110 and a machining subsystem 120. Other subsystems and other configurations may be used herein.

The thermal inspection subsystem 100 may inspect a number of hot gas path components or other types of machine components 130 with multiple cooling film holes 140, multiple internal passages, and other types of internal configurations. Examples of the components 130 may include film cooled, hot gas path components such as stationary vanes (nozzles), turbine blade (rotors), combustion liners, other combustion system components, transition pieces, shrouds, and the like.

The thermal inspection subsystem 110 may include a fluid source 150. The fluid source 150 may be configured to supply a hot flow and a cold flow, indirectly or directly, to at least one internal passage of the component 130. As used herein, the term "fluid" should be understood to encompass liquids and gases. Example fluids may include compressed gases, such as compressed air, nitrogen, steam, water, and any Newtonian fluid. Likewise, the terms "hot" and "cold" are merely used in a relative sense and do not indicate specific values. For the example arrangement shown in FIG. 1, the fluid source 150 may be a source of shop air, i.e., "cold" air at ambient conditions within the assembly facility or other location with the thermal inspection and machining system 100 housed therein.

The thermal inspection subsystem 110 further may include an imager 160. The imager 160 may be configured to capture a time series of images corresponding to a transient thermal response of the component 130 to the hot and cold flows therethrough. The thermal response corresponds to a number of intensity or temperature values for an external surface of the component 130. The intensity values may be correlated with temperature values so as to determine the temperature. A number of imagers 160 may be employed, including but not limited to, infrared detection devices such as an infrared camera 170. By way of example, the infrared camera 170 may be a FLIR SC4000 infrared camera 16 with InSb detector. The camera 170 nominally operates in about the 3-5 micron wavelength range and may have a filter that further narrows the range to about 3.9-5. Other examples of the imager 160 may include actuating pyrometers and single point pyrometers. Other types of imaging equipment and other configurations may be used herein.

The thermal inspection subsystem 110 further may include a manipulator 180. The manipulator 180 may be configured to control and automate movement of the imager 160 and/or the component 130 relative to the other. The manipulator 180 may include a robotic arm 190 or other types of automation means. For example, the imager 160 may be mounted to a FANUC LR Mate 200 iC 6 axis robotic arm 190. The robotic arm 190 may be mounted to a base, which may be fully enclosed with appropriate safety interlocks. Other types of positioning equipment and other configurations may be used herein.

The thermal inspection subsystem 110 further may include at least one flow meter 200 configured to measure the warm and cool flows supplied to the component 130. Depending on the specific implementation, the flow may switch from heating to cooling or from cooling to heating. Examples of the flow meter 200 may include sonic nozzles, Coriolis meters, laminar flow meters, orifice plates, subsonic Venturis, and the like. Other types of flow control equipment and other configurations also may be used herein.

The thermal inspection subsystem 100 further may include a number of air supply lines 205. In this example, at least one cold air line 210 and at least one hot air line 220 may be used. The cold air line 210 may supply the shop air while the hot air line 220 provides heated air. The hot air line 220 thus may include a heater 230 therein or thereabout. The heater 230 may be a mesh heater such as Nichrome V wire mesh 30 connected to a DC power supply (not shown) with programmable logic to provide the desired heating transient profile. Other types of heaters 230 may be used herein. A flow director 240 may direct the flow of air from the flow meter 200 to either the cold air line 210 or the hot air line 220. The flow director 240 may be a pneumatic three-way valve actuated by a solenoid valve. Other types of valves and air supply equipment in other configurations may be used herein.

The component 130 to be inspected may be positioned within a standard air flow fixture 250. The air fixture 250 may be similar to that currently used to determine if a component meets film hole air flow specifications and the like. The air fixture 250 seals the bottom of the component 130 and allows air flow to the interior passages from an internal plenum 260 in communication with the cold air line 210 and the hot air line 220. Other types of support equipment and other configurations may be used herein.

The thermal inspection subsystem 110 further includes at least one pressure sensor 270 for measuring the pressure within the plenum 260 and at least one temperature sensor 280 for measuring the temperature of the fluid within the plenum 260. Additional pressure sensors 270 and temperature sensors 280 also may be positioned. about the flow meter 200 and elsewhere. Other types of sensors and other types of equipment and configurations may be used herein.

The thermal inspection subsystem 110 further may include a processor 290 in communication with the imager 160 and the other devices used herein. The processor 290 may be configured to determine a transient thermal response of the component 130 and compare the transient thermal response with one or more predetermined or baseline values or with an acceptable range of values to determine if the component 130 meets a desired specification as will be described in more detail below. The processor 290 also may be operatively connected to the pressure and temperature sensors 270, 280 and to the flow meter 200. The processor 290 further may be configured to determine a flow rate though at least one of the internal passages based on the pressure and temperature within the plenum 260 and on the mass flow rate measured by flow meter 200. Specifically, the processor 290 may be configured to normalize the measured mass flow rate, pressure, and temperature values to standard conditions and to compare the standardized mass flow rate, pressure, and temperature values to respective baseline values to determine whether the component 130 meets a desired specification.

The component 130 may be loaded into the air fixture 250 with the plenum 260 therein. A series of automated steps may lock the component 130 in place and establish the desired air mass flow rate therethrough via the flow meter 200 and the pressure sensors 270. The infrared camera 170 mounted on the robotic arm 190 may be positioned at various locations to inspect the film holes 140 on the component 130. The camera 170 may be triggered to record the surface temperature response at the desired position as the component 130 undergoes a brief heating transient using the heater 230 in the hot air line 220. The hot air provides an approximate step change in temperature. A cooling transient then occurs as the heater 230 is turned off while cold shop air is sent to the plenum 260 via the cold air line 210.

Image processing algorithms may be used to identify the pixels defining each film hole 140. Specifically, the processor 290 may be configured to determine the transient thermal response by interrogating a second derivative of the intensity or temperature values one or more appropriate times during the transient. A first derivative also may be used. The processor 290 may be configured to perform the comparison by comparing the derivative of the intensity or temperature values with the one or more predetermined or baseline values or with the acceptable range of values to determine if the component 130 meets the desired specification. Typically, each of the images corresponds to a number of pixels and the processor 290 may be further configured to identify respective locations of the film holes 140 on the external surface of the component 130 based on the relative intensities of the pixels in the images and the like. Generally described, the infrared camera 170 measures and images the emitted infrared radiation from an object over a specified wavelength range. The intensity or magnitude of that radiation is dependent on many factors including emissivity, surrounding reflections, and surrounding atmospheric conditions.

With an open film hole 140, the second derivative peak magnitude at the transition from hot to cold air generally is a high absolute value. Factors, such as where the film hole 140 is located, can affect this generalization. Each film hole 140 may have a unique response to the thermal transient that must be characterized. A blocked film hole 140 loses the additional cooling benefit of convection and relies only on conduction, thus experiencing a reduced magnitude of second derivative in temperature of or intensity as compared to an open film hole 140.

The machining subsystem 120 of the imaging and machining system 100 may include a machining device 300. The machining device 300 may be a drilling device 310. The drilling device 310 may be a laser drill, EDM (Electrodischarge Machining), a mechanical drill, electro-chemical drilling, abrasive liquid jet drilling, CNC milling (Computer Numerical Control), and the like. The drilling device 310 or other type of machining device 300 may be a multi-axis device. Other types of machining devices 300 may be used herein.

The drilling device 310 or other type of machining device 300 may be mounted on the robotic arm 190 of the manipulator 180 or on a similar type of positioning device. The drilling device 310 also may be in communication with the processor 290. The drilling device 310 drills the film holes 140 within the component 130. Other types of holes or other operations may be used herein. The drilling device 310 may need one or more datums on the component 130 and/or on the air fixture 250 for accurate positioning. At least a known spatial relationship generally is required between the drilling device 310 and the component 130.

In use, the thermal inspection subsystem 110 and the machining subsystem 120 of the thermal imaging and machining system 100 provide the film holes 140 as well as film hole breakthrough detection and verification. An incorrectly drilled hole 140 thus may be corrected in-situ by combining these subsystems 110, 120. Specifically, the presence of a quality film hole 140 that meets specifications may be discerned through the registration of a proper infrared signal and analysis with an expected increase in the airflow rate over the previous hole drilling state.

Each film hole 140 or rows of film holes 140 may be inspected in an automated fashion immediately after drilling by the drilling device 310. Room temperature shop ("cold") air may be introduced into the component 130 via the flow meter 200 and the cold air line 210. After the hole 140 is drilled, a known or expected increase in the airflow should be observed over the previous hole drilling step provided that the same supply pressure was maintained or re-established via the pressure sensors 270 and the processor 290. "Hot" air via the hot air line 220 and the heater 230 may be briefly introduced to the component 130 followed by the cold room temperature shop air via the cold air line 210 and the flow director 240. The temperature transient may be recorded with the infrared camera 170. In other words, the thermal response of the component to a transient condition created by a controlled flow of fluid at a temperature differing from the initial temperature is evaluated. The airflow and infrared measurements thus verify the presence of a properly drilled and flowing film hole 140 (subject to internal geometric influences and the like). Changes in the airflow rate and supply pressure in combination with the infrared data thus provide breakthrough detection. Other transients also may be used.

Figure 2:
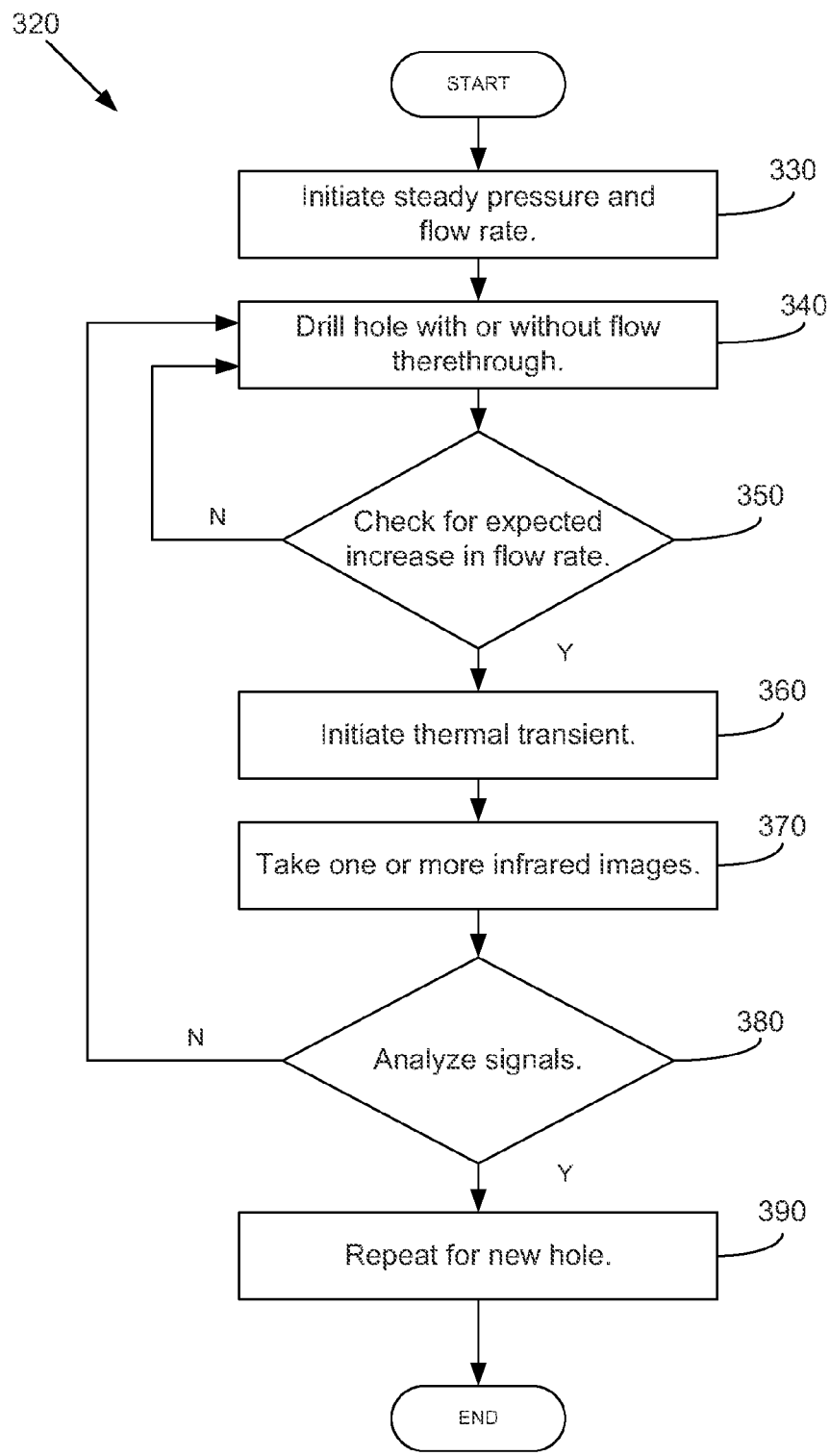
FIG. 2 is a flow chart of an example of the methods steps in the use of the thermal inspection and machining system as may be described herein.

FIG. 2 shows a flow chart 320 with a number of high level method steps in an example of the use of the thermal imaging and machining system 100. At step 330, the thermal inspection subassembly 110 maintains a steady or at least a repeatable pressure and/or flow rate into the components 130 as measured by the flow meter 200 and the pressure sensors 270. A steady flow rate or pressure is considered to be constant or repeatable to within acceptable accuracy and uncertainty limits associated with typical instrumentation and measurement devices. At this point, the flow data may be recorded. and the flow may continue or cease depending upon the drilling method and equipment used. At step 340, the machining subassembly 120 drills a film hole 140 with the drilling device 310 or modifies an existing film hole 140. At step 350, the processor 290 checks for an inspected increase in the flow rate via the flow meter 200 and/or a pressure drop via the pressure sensors 270 based upon the continued flow or a re-established flow. An expected change indicates that a proper film hole 140 has been drilled such that the method continues at step 360. If no change (no breakthrough) or less of a change (an improperly drilled hole) is detected, the method may return to step 340 for continued.

At step 360, the thermal imaging subassembly 110 initiates a thermal transient by flowing hot air via the hot air line 220 and the heater 230 into the plenum 260 and the film holes 140 of the component 130. Cold air is then flowed through the cold air line 210 and into the plenum 260 and the film holes 140 of the component 130. The infrared camera 170 then takes one or more images of the film hole or holes 140 in question at step 370 and the intensity is determined by the processor 290 at step 380. If the signals meet predetermined or benchmark expectations or a range of expectations (a properly drilled hole), then the process may be repeated for a new film hole 140 at step 390 or the process may return to step 340 for further drilling. The method then ends. Other steps may be used herein in any desired order. It also should be recognized that the steps of flowing 350 and thermal transient 360 may be repeated as desired at other intermediate points in the processing of the component 130 and are not limited to those depicted in FIG. 2. It should further be recognized that while a heating and then a cooling of the component have been described, a thermal transient also may be obtained through a cooling and then a heating of the component.

The thermal inspection subsystem 110 may be fully automated and hence faster than current inspections systems with improved accuracy. Given such, the thermal inspection subsystem 110 thus allows an operator to perform other tasks so as to increase production throughput while optionally creating an archive of all inspected components. Film holes 140 that are identified as needing rework may be automatically corrected via the machining subsystem 120.

The thermal inspection and machining system 100 thus offers potential cost and productivity savings for production shops for inspecting gas turbine components in regards to airflow design specifications and open hole inspection. Savings may be realized in the reduction of equipment expenditures and tabor costs. Infrared pin-check eliminates laborious and manual pin-checking and visual water flow inspections. Operators typically may spend five to ten minutes inspecting a single component. With the automation of infrared pin-check, that time can be reallocated to other production areas.

Other benefits of thermal inspection and machining system 100 include the fact that the infrared pin-check method provides a quantitative measurement to the openness of a hole, whereas the pin-check and water flow operations are qualitative and subject to operator discretion. in addition, the infrared pin-check readings may be stored electronically, whereas the pin-check and water flow typically are not used to create a database to monitor inspection and manufacturing quality.

It should be apparent that the foregoing relates only to certain embodiments of the present application and that numerous changes and modifications may be made herein by one of ordinary skill in the art without departing from the general spirit and scope of the invention as defined by the following claims and the equivalents thereof.

We claim:

1. An integrated thermal imaging and machining system for a machine component, comprising:
a machining subsystem;
the machining subsystem comprising a machining device for drilling one or more holes in the machine component; and
a thermal inspection subsystem positioned about the machining subsystem;
the thermal inspection subsystem comprising an imager, one or more fluid supply lines, and one or more flow meters and one or more pressure sensors positioned within the one or more fluid supply lines,
wherein the thermal inspection subsystem and the machining subsystem are integrated and associated with each other for in-situ drilling and inspection of the holes, such that further operation of the machining subsystem is continued based on a thermal response of the one or more holes in the machine component as determined by the thermal inspection subsystem.

2. The thermal imaging and machining system of claim 1, wherein the thermal inspection subsystem comprises an air fixture in fluid communication with the one or more fluid supply lines.

3. The thermal imaging and machining system of claim 2, wherein the air fixture comprises an air plenum in fluid communication with the machine component.

4. The thermal imaging and machining system of claim 1, wherein the one or more fluid supply lines comprise a plurality of fluid supply lines and the plurality of fluid supply lines comprise a hot air line and a cold air line.

5. The thermal imaging and machining system of claim 4, wherein the hot air line comprises a heater positioned thereabout.

6. The thermal imaging and machining system of claim 4, wherein the thermal imaging subsystem comprises a flow director in fluid communication with the hot air line and the cold air line.

7. The thermal imaging and machining system of claim 1, wherein the imager comprises an infrared camera.

8. The thermal imaging and machining system of claim 1, wherein the thermal imaging subsystem comprises a manipulator with the imager positioned thereon.

9. The thermal imaging and machining system of claim 8, wherein the manipulator comprises a robotic arm.

10. The thermal imaging and machining system of claim 1, wherein the machining device comprises at least one of a laser drilling device, electrodischarge machining device, mechanical drilling device, electro-chemical drilling device, abrasive liquid jet drilling device, and computer numerical control milling device.

11. The thermal imaging and machining system of claim 1, further comprising a processor and wherein the processor determines the thermal response by interrogating a derivative of one or more intensity or temperature values captured by the imager due to a transient condition.

12. A method of machining and inspecting a machine component, comprising:
flowing a steady flow rate and pressure of a fluid through the machine component;
drilling at least one hole within the machine component;
determining whether a change in the flow rate and the pressure has been detected and continuing the drilling if the change in the flow rate and the pressure has not been detected;
flowing the fluid at a first temperature and then at a second temperature through the machine component;
imaging the at least one hole within the machine component; and
determining if a thermal response of the at least one hole within the machine component meets a predetermined range of values and continuing the drilling if the thermal response does not meet the predetermined range of values.

13. The method of claim 12, wherein the step of determining the thermal response comprises interrogating a derivative of one or more intensity or temperature values captured in the imaging step.

14. The method of claim 12, further comprising the step of archiving a number of images produced in the imaging step.

15. An integrated thermal imaging and machining system for a hot gas path component, comprising:
a machining subsystem;
the machining subsystem comprising a drilling device for drilling one or more holes in the hot gas path component; and
a thermal inspection subsystem positioned about the machining subsystem;
the thermal inspection subsystem comprising an infrared camera, a hot air line, a cold air line, and one or more flow meters and one or more pressure sensors positioned within the hot air line, and the cold air line,
wherein the thermal inspection subsystem and the machining subsystem are integrated and associated with each other for in-situ drilling and inspection of the holes, such that further operation of the machining subsystem is continued based on a thermal response of the one or more holes in the machine component as determined by the thermal inspection subsystem.

16. The thermal imaging and machining system of claim 15, wherein the thermal imaging subsystem comprises a manipulator with the imager positioned thereon.

17. The thermal imaging and machining system of claim 15, further comprising a processor and wherein the processor determines the thermal response by interrogating a second derivative of one or more intensity or temperature values captured by the imager due to a transient condition.

18. The thermal imaging and machining system of claim 1, further comprising at least one processor operatively connected to the imager, the one or more flow meters and one or more pressure sensors, and the drilling device.

* * * * *